(12) United States Patent
Peng et al.

(10) Patent No.: US 11,571,133 B2
(45) Date of Patent: Feb. 7, 2023

(54) TECHNOLOGIES FOR MONITORING HEALTH-RISK CONDITION OF USER

(71) Applicant: INTEL CORPORATION, Santa Clara, CA (US)

(72) Inventors: Tao Peng, Shanghai (CN); Zhen Zhou, Shanghai (CN); Ke Han, Shanghai (CN)

(73) Assignee: Intel Corporation, Santa Clara, CA (US)

( * ) Notice: Subject to any disclaimer, the term of this patent is extended or adjusted under 35 U.S.C. 154(b) by 286 days.

(21) Appl. No.: 16/642,561

(22) PCT Filed: Sep. 30, 2017

(86) PCT No.: PCT/CN2017/104825
§ 371 (c)(1),
(2) Date: Feb. 27, 2020

(87) PCT Pub. No.: WO2019/061418
PCT Pub. Date: Apr. 4, 2019

(65) Prior Publication Data
US 2020/0214647 A1 Jul. 9, 2020

(51) Int. Cl.
*A61B 5/02* (2006.01)
*A61B 5/021* (2006.01)
(Continued)

(52) U.S. Cl.
CPC .............. *A61B 5/02* (2013.01); *A61B 5/021* (2013.01); *A61B 5/02433* (2013.01);
(Continued)

(58) Field of Classification Search
CPC .... A61B 5/00; A61B 5/01; A61B 5/02; A61B 5/024; A61B 5/0245; A61B 5/0402;
(Continued)

(56) References Cited

U.S. PATENT DOCUMENTS

| 2016/0164559 A1* | 6/2016 | Kim | ........................ H04W 76/50 |
| | | | 455/575.6 |
| 2016/0262608 A1* | 9/2016 | Krueger | ................. G16H 50/20 |

(Continued)

FOREIGN PATENT DOCUMENTS

| CN | 101046557 | 10/2007 |
| CN | 102614661 | 8/2012 |

(Continued)

OTHER PUBLICATIONS

NPL Search (May 5, 2022).*
PCT Search Report and Written Opinion prepared for PCT/CN2017/104825, completed Jun. 14, 2018.

*Primary Examiner* — Van T Trieu

(57) ABSTRACT

Technologies for monitoring a health-risk condition of a user include a virtual reality compute device having one or more near infrared (NIR) sensors. The virtual reality compute device presents a virtual reality (VR) presentation to the user. The virtual reality compute device produces sensor data through the one or more NIR sensors that is indicative of a heart rate of the user and a blood pressure of the user while the VR presentation is presented to the user. The virtual reality compute device determines whether the user is in a health-risk condition based on a comparison of the heart rate of the user to a heart rate safety threshold and a comparison of the blood pressure of the user to a blood pressure safety threshold. The virtual reality compute device performs a health-risk condition response in response to a determination that the user is in the health-risk condition.

25 Claims, 7 Drawing Sheets

(51) Int. Cl.
    *A61B 5/024*     (2006.01)
    *A61B 5/00*     (2006.01)
    *G08B 21/04*     (2006.01)

(52) U.S. Cl.
    CPC ............ *A61B 5/746* (2013.01); *A61B 5/7246* (2013.01); *A61B 5/7275* (2013.01); *A61B 5/7445* (2013.01); *G08B 21/0453* (2013.01)

(58) Field of Classification Search
    CPC .. A61B 5/11; A61B 3/11; A61B 3/112; A61B 3/113; A61B 3/14; G06F 3/01; G06F 3/012; G06F 3/013; G06K 9/00; H04B 1/3827; H04W 4/02; H04W 4/12
    See application file for complete search history.

(56) References Cited

U.S. PATENT DOCUMENTS

2017/0325700 A1* 11/2017 Lane .................. A61N 1/36053
2020/0305708 A1* 10/2020 Krueger .................. G06F 3/012

FOREIGN PATENT DOCUMENTS

| | | |
|---|---|---|
| CN | 106339084 | 1/2017 |
| CN | 106502411 | 3/2017 |
| CN | 206161960 | 5/2017 |

* cited by examiner

TECHNOLOGIES FOR MONITORING HEALTH-RISK CONDITION OF USER

CROSS REFERENCE TO RELATED APPLICATIONS

The present application is a national stage entry under 35 USC § 371(b) of International Application No. PCT/CN2017/104825, filed Sep. 30, 2017.

BACKGROUND

Popularity of virtual reality devices is increasing as it is applied to content viewable by smartphones, video games implementing a virtual reality headset, and the like. The content presented by these virtual reality devices range from a variety of genres. The spectrum of content can include movies (e.g., action movies), games (e.g., first-person shooter games), and/or other active content.

However, some content presented by virtual reality devices, such as very active or abrupt content (e.g., a scare scene in a horror movie), can cause some users to react negatively if not properly monitored. For example, users who are susceptible to being scared by horror movies or the like may have had reactions while using the virtual reality devices. Such users may, for example, develop a feeling of being trapped and accidentally hurt themselves or others nearby while operating the virtual reality device. In addition, extreme content may place some users in a condition for a health risk. That is, in certain situations users could potentially experience heart attacks from the use of the virtual reality device.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
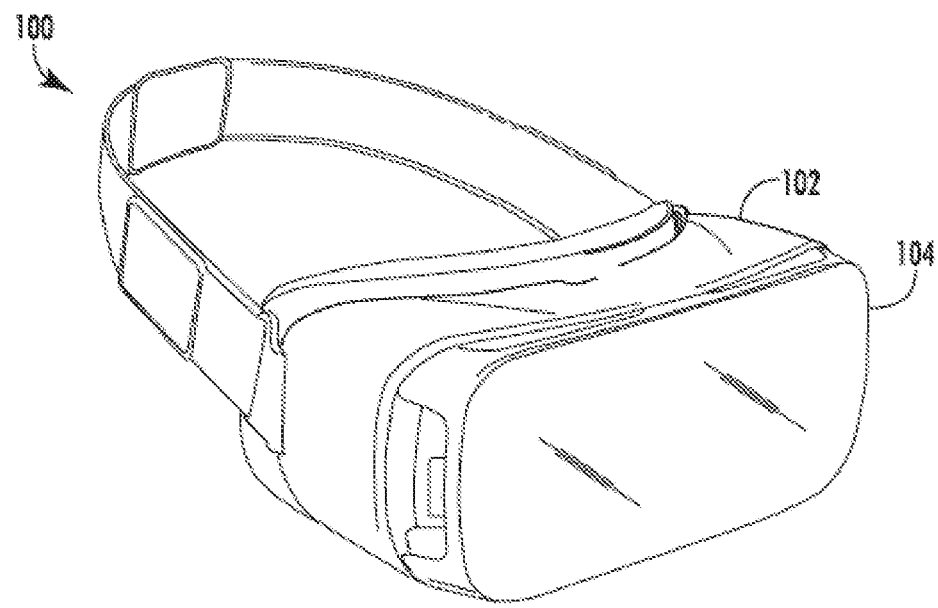
FIG. 1 is an example depiction of at least one embodiment of a virtual reality (VR) system for monitoring a health-risk condition of a user.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a virtual reality (VR) system 100 for monitoring a health-risk condition of a user includes a virtual reality compute device 102 configured to monitor the health-risk condition of the user and a virtual reality generation device 104 configured to present a VR presentation to the user. In some embodiments, the virtual reality compute device 102 and the virtual reality generation device 104 may be integrated as a single device. However, in other embodiments, the virtual reality compute device 102 and the virtual reality generation device 104 may be separate devices that may couple together or otherwise operate together to present a VR presentation to a user. For example, the virtual reality compute device 102 may be embodied as a head-worn compute device and the virtual reality generation device 104 may be embodied as a separate display device (e.g., the user's smartphone).

Figure 2:
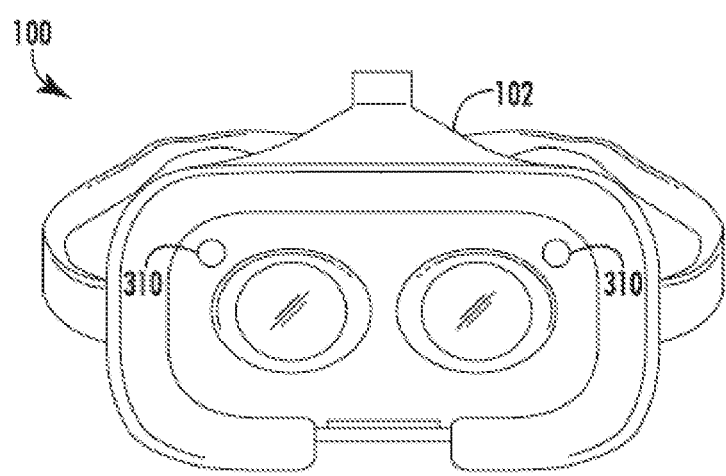
FIG. 2 is another view of the example of the at least one embodiment of the VR system of FIG. 1.

In use, as discussed in more detail below, the virtual reality compute device 102 monitors the health-risk condition of the user by using near infrared (NIR) sensors 310 as shown in FIG. 2 to produce sensor data indicative of a heart rate of the user and a blood pressure of the user while the virtual reality generation device 104 outputs the VR presentation to the user. The NIR sensors 310 may be coupled to the VR system 100 in such a way that they do not obstruct the field of vision of the user viewing the VR presentation. The inclusion of the NIR sensors 310 may improve the viewer experience of the user while adding additional safety measures, such as monitoring for a health-risk condition. The health-risk conditions that the VR system 100 may monitor may include a potential heart attack, loss of consciousness, and/or other health-risk conditions users may experience from viewing a VR presentation. For example, the nature of the VR content may be extreme in nature and could potentially frighten or overexcite the user of the VR system 100.

As described in more detail below, the virtual reality compute device 102 may use the NIR sensors 310 to perform measurements on, for example, the user's eyes to produce the sensor data. The virtual reality compute device 102 may subsequently perform a comparison between the sensor data and a safety threshold to determine whether the user is in a health-risk condition. For example, the virtual reality compute device 102 may determine that a particular user has an elevated heart rate that is unusual and identify that the user is in a health-risk condition, such as potentially having a heart attack. As such, the virtual reality compute device 102 may promptly respond to the determination that the user is in a health-risk condition and perform a health-risk condition response, which may include generating a warning or, in some cases, turning off the VR presentation thereby improving the safety of the user through the implementation of such safety responses. As such, the virtual reality compute device 102 improves upon the user experience by ensuring the user is at a comfortable level throughout viewing the VR presentation.

Figure 3:
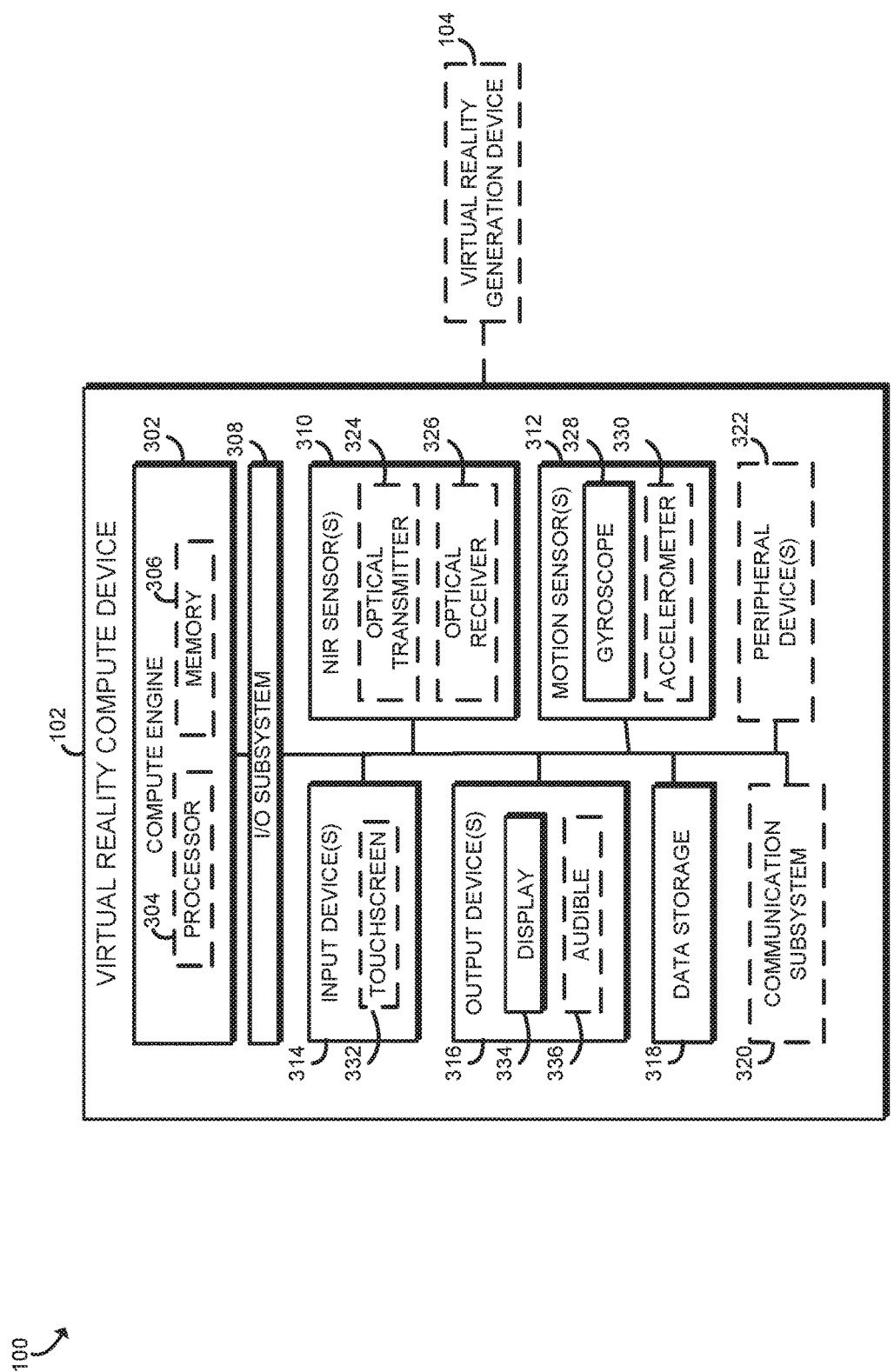
FIG. 3 is a simplified block diagram of at least one embodiment of a virtual reality compute device of the VR system shown in FIG. 1.

Referring now to FIG. 3, as discussed above, the VR system 100 include the virtual reality compute device 102 and the virtual reality generation device 104, which may or may not be integrated together. In the illustrative embodiment, the virtual reality compute device 102 is configured to monitor for a health-risk condition of a user as discussed above. The virtual reality compute device 102 may be embodied as any type of compute device capable of being worn or carried by a user to present a VR presentation to the user and performing the functions described herein. For example, the virtual reality compute device 102 may be embodied as a virtual reality headset, a headset in combination with a smart phone, smart glasses, a smart phone, accessories, and/or another computing device capable of being worn by the user to present a VR presentation to the user. In other embodiments, the virtual reality compute device 102 may be embodied as a tablet computer, a laptop computer, a notebook, a netbook, an Ultrabook™, a smart device, a personal digital assistant, a mobile Internet device, a gaming console, and/or any other computing device capable of generating a VR presentation for the user. Depending on form factor, the virtual reality compute device 102 may include a strap and/or other coupling mechanisms to allow attachment to the user. Additionally, in some embodiments, the virtual reality compute device 102 may include other coupling mechanisms (e.g., clips, straps, etc.) to allow the coupling of a separate virtual reality generation device 104 (e.g., a smartphone) to the virtual reality compute device 102.

As shown in FIG. 3, the illustrative virtual reality compute device 102 includes a compute engine 302, an input/output ("I/O") subsystem 308, one or more NIR sensor(s) 310, one or more motion sensor(s) 312, one or more input devices 314, one or more output devices 316, and a data storage device 318. In some embodiments, the virtual reality compute device 102 may also include a communication subsystem 320 and peripheral devices 322. Of course, the virtual reality compute device 102 may include other or additional components, such as those commonly found in a typical compute device, in other embodiments. Additionally, in some embodiments, one or more of the illustrative components may be incorporated in, or otherwise form a portion of, another component.

The compute engine 302 may be embodied as any controller, functional block, digital logic, or other component, device, circuitry, or collection thereof capable of performing the functions described herein. In some embodiments, the compute engine 302 may include a processor 304 and a memory 306. In such embodiments, the processor 304 may be embodied as any type of processor capable of performing the functions described herein. For example, the processor 304 may be embodied as a single or multi-core processor(s), digital signal processor, microcontroller, or other processor or processing/controlling circuit. Similarly, the memory 306 may be embodied as any type of volatile or non-volatile memory or data storage capable of performing the functions described herein. In operation, the memory 306 may store various data and software used during operation of the virtual reality compute device 102 such as operating systems, applications, programs, libraries, and drivers. The memory 306 is communicatively coupled to the processor 304 via the I/O subsystem 308, which may be embodied as circuitry and/or components to facilitate input/output operations with the processor 304, the memory 306, and other components of the virtual reality compute device 102. For example, the I/O subsystem 308 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 308 may form a portion of a system-on-a-chip (SoC) and be incorporated, along with the processor 304, the memory 306, and other components of the virtual reality compute device 102, on a single integrated circuit chip. In some embodiments, the memory 306, or portions of the memory 306 may be incorporated into the processor 304.

The NIR sensor(s) 310 may be embodied as any one or more sensors capable of producing sensor data indicative of a heart rate of the user and a blood pressure of the user. For example, in some embodiments, the NIR sensor(s) 310 may include an optical transmitter 324 and an optical receiver 326 configured to produce sensor data indicative of a heart rate of the user and a blood pressure of the user based on optical signals transmitted through the eyes or skin of the user. In other embodiments, additional or other sensors may be included in the virtual reality compute device 102 to produce similar or other sensor data indicative of the heart rate of the user and a blood pressure of the user.

The motion sensor(s) 312 may be embodied as any one or more sensors capable of generating or producing sensor data indicative of movement of the user wearing and/or using the virtual reality compute device 102. The sensor data may be embodied as any type of data capable of indicative of a body movement of the user. For example, the sensor data may be indicative of movement of the user's torso, arms, head, and/or other body part. For example, the sensor data may be indicative of movement of the user's body from an initial position to a measured position. As such, in some embodiments, the sensor data produced by the motion sensor(s) 312 may be indicative of an angle of the direction of the user in relation to the original direction a user was facing during the start of the VR presentation. In such scenarios, the angle may be set to 0 degrees when the user has not moved in any direction from the initial position. In addition, the angle may increase either clockwise or counterclockwise. Furthermore, in some embodiments, the sensor data may be indicative of a physical location of the user in relation to the original location of the user at the start of the VR presentation. That is, the sensor data may identify, for example, that the user has moved 10 feet forward in relation to the original location of the user. To do so, in the illustrative embodiment, the motion sensor(s) 312 includes one or more gyroscopes 328. Additionally or alternatively, the motion sensor(s) 312 may include one or more accelerometers 330. In other embodiments, additional or other sensors may be included in the virtual reality compute device 102 to generate sensor data indicative of the position of the user relative to the starting position of the user.

The input device(s) 314 may be embodied as any one or more devices capable of receiving an interaction from a user of the virtual reality compute device 102 and providing an input to the virtual reality compute device 102 based on such interaction. In some embodiments, the input device(s) 314 may be embodied as, or otherwise include, a touchscreen 332, which may receive input from the user based on a tactile interaction. Of course, the input device(s) 314 may include additional or other types of input devices such as a physical or virtual keyboard, buttons, switches, microphones, a mouse, one or more handheld devices, joysticks, wearable devices, and so forth.

The output device(s) 316 may include, or be embodied as, any type of output device capable of providing information (e.g., the VR presentation) to the user of the virtual reality compute device 102. In the illustrative embodiment, the output device(s) 316 include a display 334. In some embodiments, the output device(s) 316 may include an audible device 336. The output device(s) 316 may include additional or other components in other embodiments. The display 334 may be embodied as any type of display capable of displaying information to the user of the hydration measurement device 102. For example, the display 334 may be embodied as a liquid crystal display (LCD), a light emitting diode (LED) display, an organic light emitting diode (OLED), a cathode ray tube (CRT) display, a plasma display, and/or other display device. Additionally, in some embodiments, the touchscreen 332 may form a portion of the display 334. The audible 336 may be embodied as any type of audio generation device, such as a speaker or annunciator, capable of producing sound. It should be appreciated that in embodiments in which the virtual reality generation device 104 is incorporated in, or otherwise forms a part of the virtual reality compute device 102, the output devices 316 may be embodied as the virtual reality generation device 104.

The data storage device 318 may be embodied as any type of device or devices configured for short-term or long-term storage of data such as, for example, memory devices and circuits, memory cards, hard disk drives, solid-state drives, non-volatile flash memory, or other data storage devices.

In some embodiments, the virtual reality compute device 102 may also include a communication subsystem 320. The communication subsystem 320 may be embodied as any type of communication circuit, device, or collection thereof, capable of enabling communications between the virtual reality compute device 102 and other remote devices such as other virtual reality compute devices 102, a server (not shown) or other components of the virtual reality system 100. To do so, the communication subsystem 320 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

In some embodiments, the virtual reality compute device 102 may also include one or more peripheral device(s) 322. The peripheral device(s) 322 may include any number of additional peripheral or interface devices, such as other input/output devices, storage devices, and so forth. The particular devices included in the peripheral device(s) 322 may depend on, for example, the type and/or intended use of the virtual reality compute device 102.

As discussed above, in some embodiments, the VR system 100 may include a separate virtual reality generation device 104 as shown in FIG. 3 in dashed line. In such embodiments, the virtual reality generation device 104 may be coupled to the virtual reality compute device 102 via a wired or wireless connection. The virtual realtion generation device 104 may be embodied as any type of device capable of presenting a VR presentation to the user such as, for example, a smartphone, a display device, and/or other VR presentation device. As such, the virtual reality generation device 104 may include similar components as the virtual reality compute device 102 such as a compute engine, output devices, a communication subsystem, and so forth.

Figure 4:
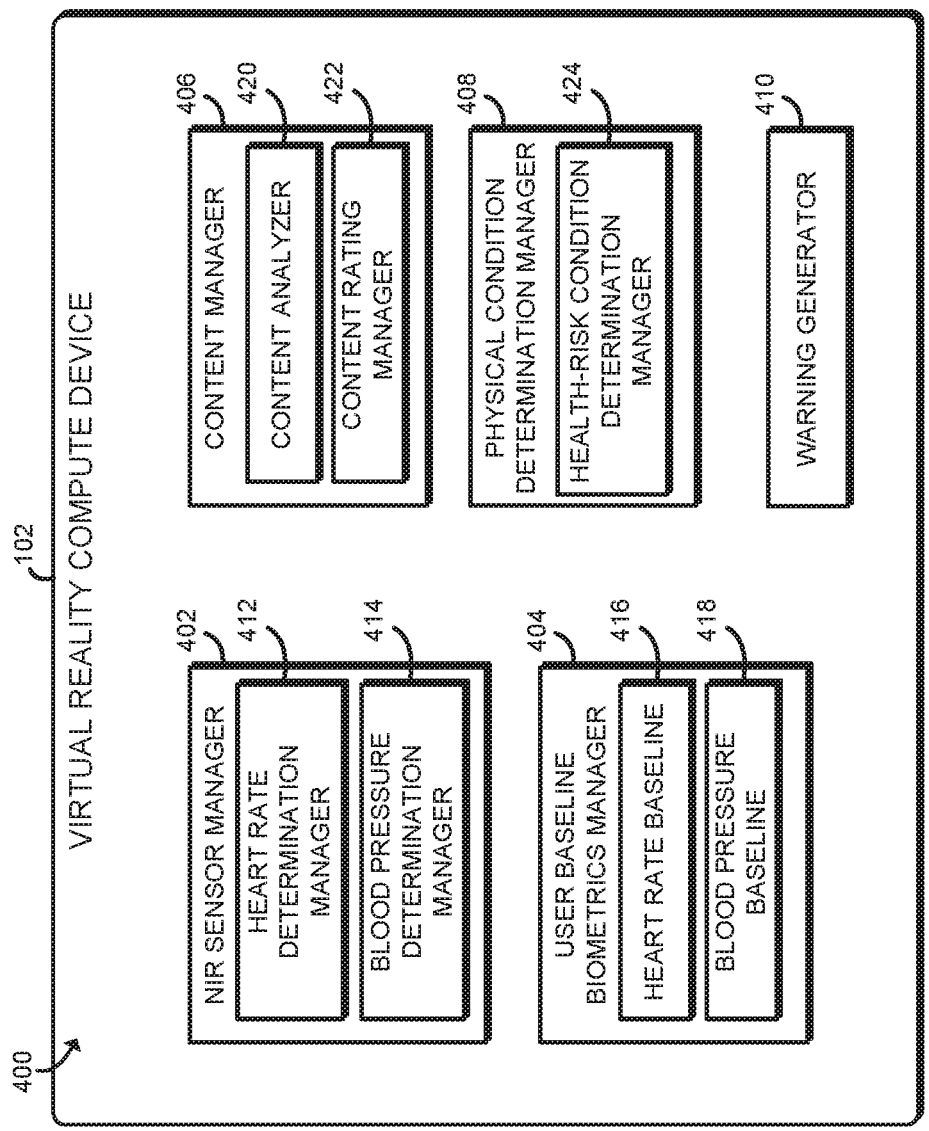
FIG. 4 is a simplified block diagram of at least one embodiment of an environment that may be established by the virtual reality compute device of FIG. 3.

Referring now to FIG. 4, in the illustrative embodiment, the virtual reality compute device 102 may establish an environment 400 during operation. The illustrative environment 400 includes a NIR sensor manager 402, a user baseline biometrics manager 404, a content manager 406, a physical condition determination manager 408, and a warning generator 410. Each of the components, logic, and other modules of the environment 400 may be embodied as hardware, firmware, software, or a combination thereof. As such, in some embodiments, one or more of the components of the environment 400 may be embodied as circuitry or collection of electrical devices (e.g., NIR sensor manager circuitry 402, user baseline biometrics manager circuitry 404, content manager circuitry 406, physical condition determination manager circuitry 408, warning generator circuitry 410, etc.). It should be appreciated that, in some embodiments, one or more of the NIR sensor manager 402, the user baseline biometrics manager 404, the content manager 406, the physical condition determination manager 408, and/or the warning generator 410 may form a portion of one or more of the compute engine 302, processor 304, memory 306, NIR sensor(s) 310, motion sensor(s) 312, and/or other components of the virtual reality compute device 102. Additionally, in some embodiments, one or more of the illustrative components may form a portion of another component and/or one or more of the illustrative components may be independent of one another. Further, in some embodiments, one or more of the components of the environment 400 may be embodied as virtualized hardware components or emulated architecture, which may be established and maintained by the processor 304 or other components of the virtual reality compute device 102.

The NIR sensor manager 402, which may be embodied as hardware, firmware, software, virtualized hardware, emulated architecture, and/or a combination thereof as described above, is configured to control the NIR sensor(s) 310 to produce sensor data indicative of the heart rate of the user and the blood pressure of the user. As described above, the virtual reality compute device 102 uses the NIR sensor(s) 310 in order to measure the heart rate and blood pressure of the user while presenting the VR presentation to the user to collect sensor data in real time to determine the condition of the user during the VR presentation. In the illustrative embodiment, the NIR sensor manager 402 includes a heart rate determination manager 412 and a blood pressure determination manager 414. The heart rate determination manager 412 is configured to obtain the sensor data produced by the NIR sensor(s) 310 and determine the present heart rate of the user based on the sensor data. Similarly, the blood pressure determination manager 414 is configured to obtain the sensor data produced by the NIR sensor(s) 310 and determine the present blood pressure of the user based on the sensor data. Additionally, in some embodiments, the blood pressure determination manager 414 may be configured to determine a hypertension grade based on the determined blood pressure.

The user baseline biometrics manager 404, which may be embodied as hardware, firmware, software, virtualized hardware, emulated architecture, and/or a combination thereof as described above, is configured to establish and maintain the baseline biometrics of the user of the virtual reality compute device 102. The baselines establish the safety thresholds for user operation of the virtual reality compute device 102. That is, the virtual reality compute device 102 monitors to verify that no safety threshold, based on the user's bassline biometrics, is exceeded while the user is watching the VR presentation. In the illustrative embodiment, the user baseline biometrics manager 404 includes a heart rate baseline 416 and a blood pressure baseline 418.

The heart rate baseline 416 is configured to establish the baseline for the user's heart rate. The baseline correlates to suitable heart rate ranges the user may experience during safe operation of the virtual reality compute device 102. That is, the user is at no risk of a health-risk condition during operation. To establish the baseline, the user may input values for various heart rate parameters. For example, the user may input the average resting heart rate, age, weight, gender, etc. in order for the virtual reality compute device 102 to accurately determine heart rate safety thresholds for the user to be within during operation of the virtual reality compute device 102. Subsequently to input of the heart rate parameters, the heart rate baseline 416 may establish proper heart rate safety thresholds. Furthermore, the heart rate baseline 416 may require input on the user's predisposition for a health-risk condition. For example, a user may be required to input whether or not the user has experienced a heart attack or the like. Such information allows for the virtual reality compute device 102 to be aware of additional concerns during operation of the virtual reality compute device 102 and potentially adjust thresholds to account for such health history. Alternatively to manual input of the information, the heart rate baseline 416 may retrieve data stored in the data storage 318 regarding the user's heart rate parameters or communicate with another device to retrieve the proper information to accurately determine the user's heart rate safety threshold (e.g., by communicating with a health data device of the user). In addition, the heart rate baseline 416 may update the baseline during operation of the virtual reality compute device 102 to accurately set safety thresholds. For example, if the user has to discontinue use of the virtual reality compute device 102 at any point in relation to a health-risk condition associated with an elevated heart rate, the heart rate baseline 416 may update the heart rate safety thresholds used by the virtual reality compute device 102 in response to such event.

Similarly to the heart rate baseline 416, the blood pressure baseline 418 is configured to establish the baseline for the user's blood pressure. The baseline correlates to suitable blood pressure ranges the user may experience during safe operation of the virtual reality compute device 102. For example, the range of blood pressure values may be embodied as values where the user is at no risk of a health-risk condition during operation. Similarly to the establishing the baseline for the heart rate, the user may input values for various blood pressure parameters to establish the baseline of the blood pressure of the user. For example, the user may input the average blood pressure, age, weight, gender, etc. for the virtual reality compute device 102 to accurately determine blood pressure safety thresholds for the user to be within during operation of the virtual reality compute device 102. Subsequently to input of the blood pressure parameters, the blood pressure baseline 418 may establish proper blood pressure safety thresholds. In addition, the blood pressure baseline 418 may require further input from the user on the user's predisposition for a health-risk condition. For example, whether the user has hypertension or the like. Such information may be considered because it may impact the blood pressure safety thresholds computed by virtual reality compute device 102. Alternatively to manual input of the information, the blood pressure baseline 418 may retrieve data stored in the data storage 318 regarding the user's blood pressure parameters or communicate with another device to retrieve the proper information to accurately determine the user's blood pressure safety threshold. In addition, the blood pressure baseline 418 may similarly update the baseline as the heart rate baseline 416 updates the baseline. In addition to establishing the baseline for the user's blood pressure, the blood pressure baseline 418 may also establish the baseline for the user's hypertension grade, which may be embodied as a generalization of the user's blood pressure. The use of the hypertension grade further identifies whether the user is at risk of a health-risk condition, such as a high hypertension grade. The blood pressure baseline 418 may similarly store safety thresholds for the hypertension grades as the safety thresholds for the user's blood pressure.

The content manager 406, which may be embodied as hardware, firmware, software, virtualized hardware, emulated architecture, and/or a combination thereof as described above, is configured to present and analyze the content of the VR presentation presented on the virtual reality compute device 102. For example, the content manager 406 may output the VR presentation to a display for the user to view. Furthermore, the content manager 406 analyzes the content to determine whether a user would be exposed to content that can potentially elevate the user's biometrics. For example, the content may raise the user's heart rate or blood pressure such as during a scary scene. It should be appreciated that the VR presentation may comprise content, such as movies and/or video games, that may lead to excessive user excitement and elevate the user's heart rate or blood pressure. As such, the analysis of the content allows for the virtual reality compute device 102 to take preemptive measures to ensure the user avoids a health-risk condition. To do so, in the illustrative embodiment, the content manager 406 includes a content analyzer 420 and a content rating manager 422.

The content analyzer 420 is configured to analyze the content of the VR presentation to identify risk features that will elevate the user biometrics. The risk features may include, or otherwise be embodied as, any combination of noise volume, light levels or abrupt changes in light levels, images and/or sounds, timing of presentation features, etc.

that may elevate the user biometrics, such as the user's heart rate or blood pressure. For example, if the VR content has a loud explosion with a quick flash of light, the user may be startled by the sudden change in the VR presentation. In addition, the risk features may identify dynamic events in the VR presentation through the combination of risk features. For example, dynamic events may be an event in the VR presentation that includes a figure popping out in front of the user's view within the VR presentation, like a killer in a movie jumping in front of the camera view. Other dynamic events may include suspenseful events in scary movies that may be identified by times of long darkness within the movie. By using the risk features, the content analyzer may identify moments in the VR presentation that may lead to elevation of the user biometrics. Furthermore, the content analyzer 420 may further store identified risk features as the user continues operation of the virtual reality compute device 102. That is, the content analyzer 420 may extrapolate patterns within the content of various VR presentations. For example, content analyzer 420 may identify a pattern that the user's heart rate or blood pressure increases every time the VR presentation presents a dark landscape for long periods of time for a particular genre. Furthermore, the content analyzer 420 may categorize the contents of the VR presentation to appropriately analyze the content. For example, if the VR presentation is directed to a video game that includes zombies, the content analyzer 420 would identify risk features that will elevate user biometrics. However, if the VR presentation is directed to a children's movie, the content analyzer 420 may not necessarily need to analyze the content (unless a particular user has a historical tendency to react adversely to particular features of such presentation, such as a the presence of a spider or clown in the children's movie). As such, the content analyzer 420 may be turned on and off according to a particular category.

In addition, in some embodiments, the content analyzer 420 may communicate with other virtual reality compute devices 102 or a server compiling the data from multiple virtual reality compute devices 102 to identify risk features that elevate user biometrics. For example, for a particular VR presentation, one event within the VR presentation may be identified to elevate user biometrics for a plurality of users and so will be determined to elevate the user biometrics. To perform the analyzing, in some embodiments, the content analyzer 420 may analyze future content that has not yet been presented to the user. In particular, the content analyzer 420 may apply at least one temporal window to the VR presentation to analyze sections of the VR presentation. The temporal windows may comprise, for example, the next five minutes of the VR presentation or any other suitable time frame to identify upcoming risk features that will elevate user biometrics. Alternatively, the content analyzer 420 may analyze the entirety of the VR presentation to identify risk features prior to the user starting the VR presentation.

The content rating manager 422 is configured to predict whether the risk features identified by the content analyzer 420 will elevate the user to health-risk conditions. To do so, the content rating manager 422 rates the content on how likely it is to elevate the user to the health-risk condition. For example, whether a scary moment in the VR presentation will raise the user's heart rate or blood pressure. Given that the content analyzer 420 identifies moments of the VR presentation, the content rating manager 422 may determine that the user is at a certain level and future content will elevate the user biometrics across a safety threshold during the identified moments. As such, the content rating manager 422 determines an estimated impact of the risk features to the heart rate or blood pressure of the user. In particular, in some embodiments, the content rating manager 422 may predict whether the identified risk features will elevate the user's heart rate above the heart rate safety threshold and/or elevate the user's blood pressure above the blood pressure safety threshold. The content rating manager 422 may further identify patterns for a particular user in relation to content of the VR presentation since not all users respond to similar content the same. For example, one user may be more susceptible to identified risk features if the user is particularly afraid of scary movies as compared to a horror movie enthusiast.

The physical condition determination manager 408, which may be embodied as hardware, firmware, software, virtualized hardware, emulated architecture, and/or a combination thereof as described above, is configured to determine the physical condition of the user. For example, whether the user is comfortable with the content of the VR presentation currently shown to the user. In the illustrative embodiment, the physical condition determination manager 408 includes health-risk condition determination manager 424 configured to determine whether the user is in a health-risk condition as described above. That is, the health-risk condition determination manager 424 receives data from the NIR sensor manager 402 to determine present heart rate and blood pressure and compares those values to heart rate safety thresholds and blood pressure safety thresholds established by the user baseline biometrics manager 404. If the present heart rate or blood pressure of the user exceeds the respective safety thresholds, the health-risk condition determination manager 424 determines that the user is in a health-risk condition. This may include, for example, a heart attack or some other abnormality. The health-risk condition determination manager 424 may communicate with the content rating manager 422 to properly identify situations where the user may be or will be in a health-risk condition.

The warning generator 410, which may be embodied as hardware, firmware, software, virtualized hardware, emulated architecture, and/or a combination thereof as described above, is configured to perform a health-risk condition response in response to a determination that the user is in a health-risk condition. The warning generator 410 provides a response in order to avoid or address a potential devastating health-risk condition of the user. For example, the warning generator 410 may generate a warning to notify the user of a possibility of a health-risk condition. Such a warning may occur for moments in which the user is experiencing abnormal heart rate and/or blood pressure values. Subsequent to the warning, the user may determine that he or she is still comfortable and continue the VR presentation or terminate the VR presentation. As the virtual reality compute device 102 further identifies certain patterns, the virtual reality compute device 102 may identify proper moments to notify the user. In addition to generating a warning, in some embodiments, the warning generator 410 may notify a remote compute device that the user is in a health-risk condition. Such a communication may be used for the case in which the user is unable to respond properly after the virtual reality compute device 102 determines the user is in a health risk condition. Additionally, during certain cases, the warning generator 410 may perform an emergency shutdown of the VR presentation to avoid further elevation of the user biometrics. Subsequent to the emergency shutdown, the warning generator 410 may communicate with the content manager 406 to provide a display of at least a neutral or calming presentation to deescalate the user biometrics.

Figure 5:
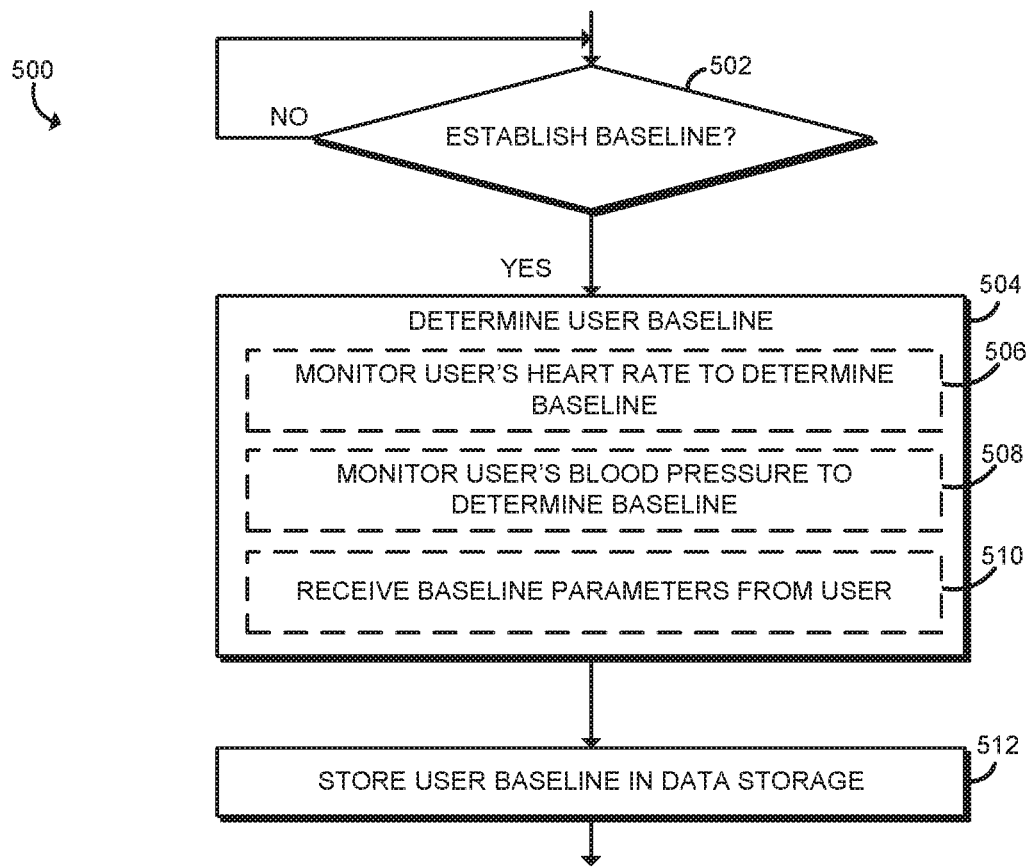
FIG. 5 is a simplified flow diagram of at least one embodiment of a method for establishing a user baseline to monitor the health-risk condition of the user that may be executed by the virtual reality compute device of FIGS. 1-4.

Referring now to FIG. 5 in use, the virtual reality compute device 102 may execute a method 500 for establishing a user baseline to monitor the health-risk condition of the user of the virtual reality compute device 102. The method 500 begins with block 502 in which the virtual reality compute device 102 determines whether the user wants to establish a baseline. To do so, the virtual reality compute device 102 may wait to receive an input from the user as described above or an initiation to retrieve appropriate data to establish a baseline. If it is determined that the user wants to establish a baseline, the method 500 advances to block 504. However, if it is determined that the user does not want to establish a baseline, the method 500 loops back to the start of block 502.

In block 504, the virtual reality compute device 102 determines the user baseline as described above. To do so, in some embodiments, in block 506, the virtual reality compute device 102 monitors the user's heart rate for a period of time while the user is performing a typical activity (e.g., just sitting). Alternatively, in some embodiments, the virtual reality compute device 102 monitors the user's heart rate while the user is viewing a VR presentation (e.g., a sample VR presentation). The heart rate baseline is to identify safety thresholds of a range of heart rate values the user comfortably experiences during viewing of a VR presentation as described above. Further, in some embodiments, in block 508, the virtual reality compute device 102 monitors the user's blood pressure as the user is performing a typical activity (e.g., just sitting). Alternatively, in some embodiments, the virtual reality compute device 102 monitors the user's blood pressure while the user is viewing a VR presentation (e.g., a sample VR presentation). Similarly to the heart rate baseline, the blood pressure baseline identifies safety thresholds of a range of blood pressure values the user comfortably experiences during viewing of the VR presentation as described above. Furthermore, the virtual reality compute device 102 may determine the hypertension grade baselines to identify hypertension grade safety thresholds as described above. Alternatively or in conjunction, in some embodiments, in block 510, the virtual reality compute device 102 receives baseline parameters from the user. This may include age, gender, weight, etc. to properly identify safety thresholds for the user biometrics as described above. In addition, the information received in block 510 may include information of whether the user is susceptible to a health-risk condition. Regardless, in block 512, the virtual reality compute device 102 stores the user baseline in a data storage 318 for subsequent access by the virtual reality compute device 102 to determine whether the user is in a health-risk condition as described above.

Figure 6:
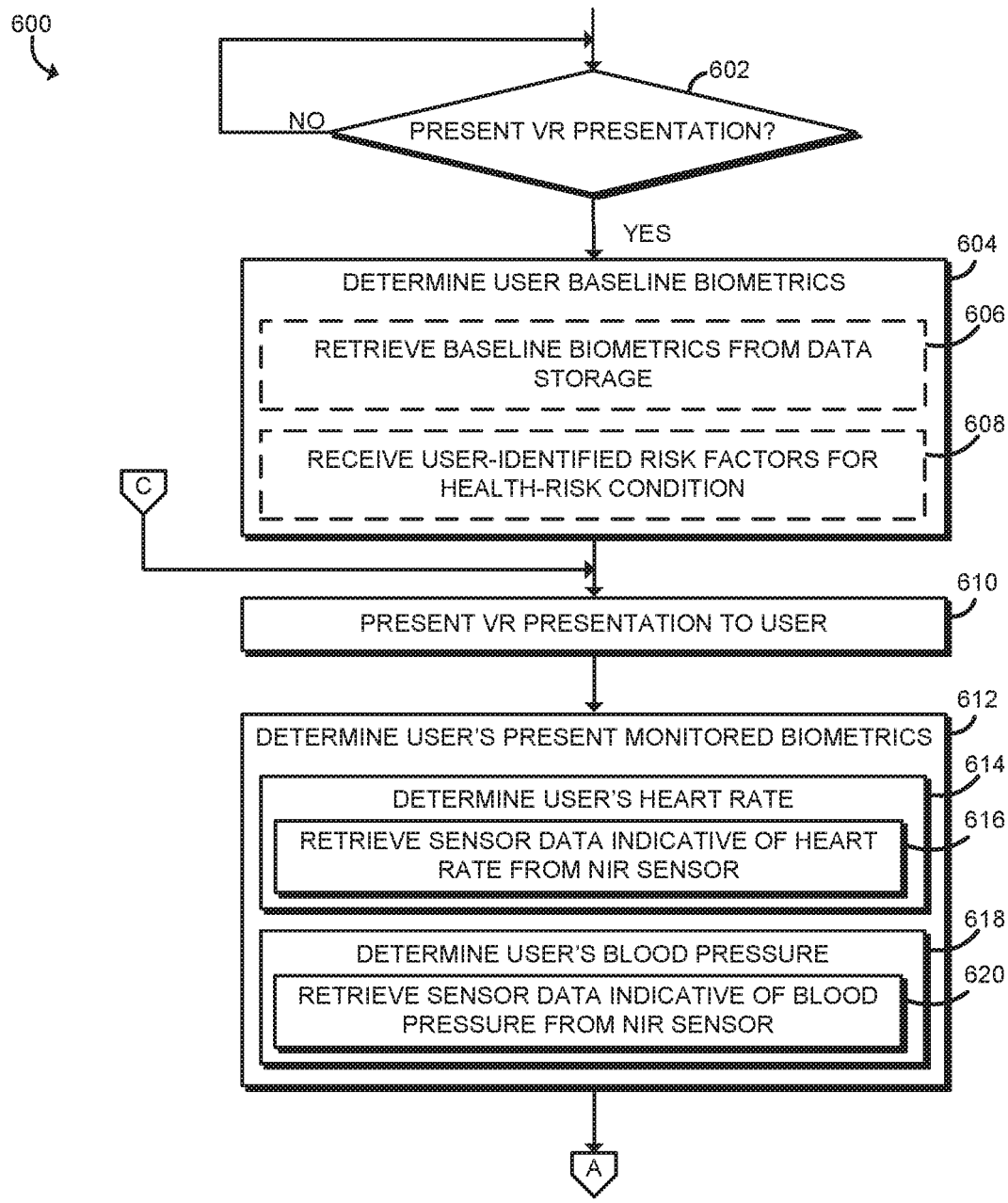
FIGS. 6-8 are a simplified flow diagram of at least one embodiment of a method for monitoring the health-risk condition of the user that may be executed by the virtual reality compute device of FIGS. 1*a*-4.
Figure 7:
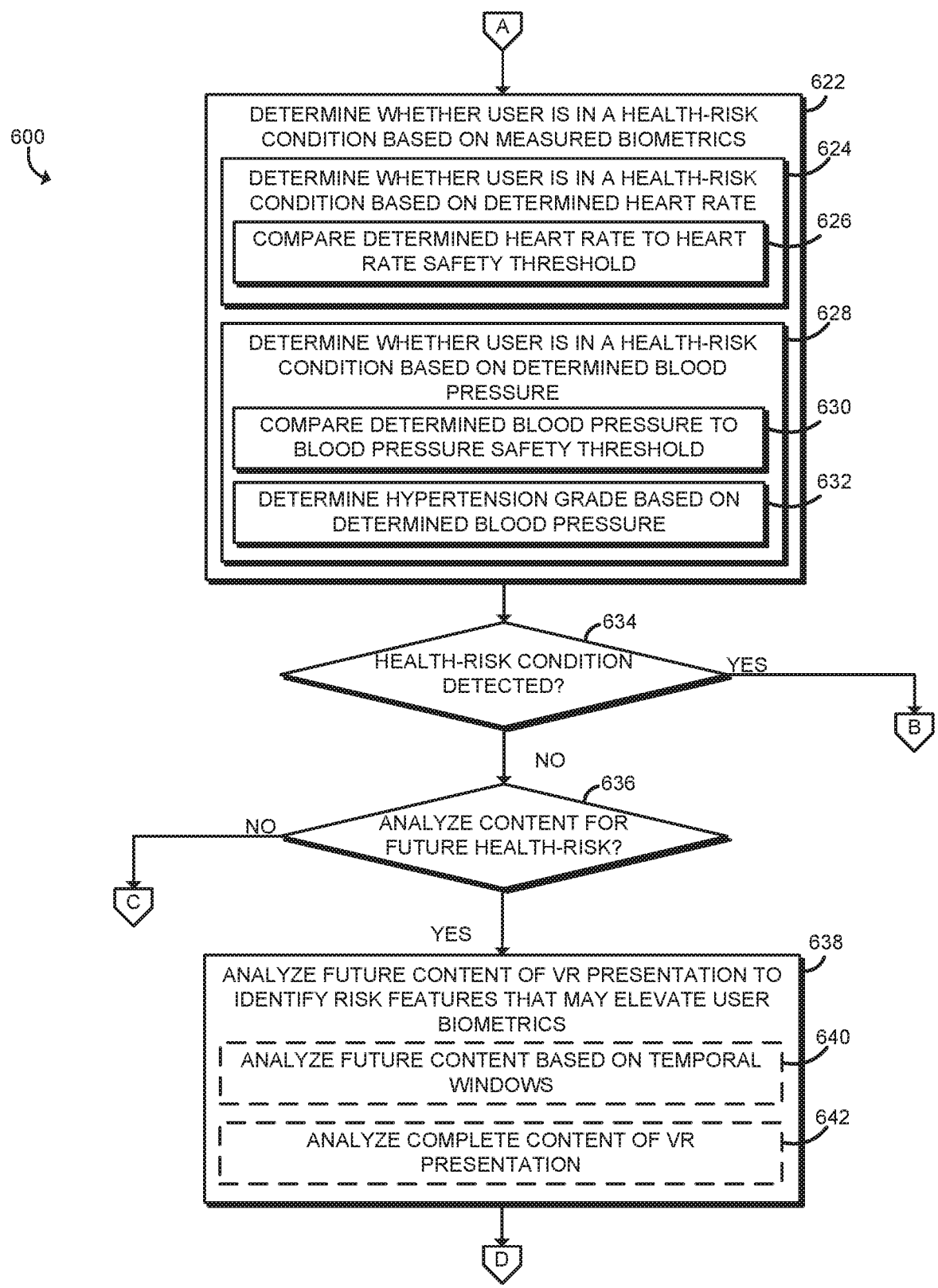
Figure 8:
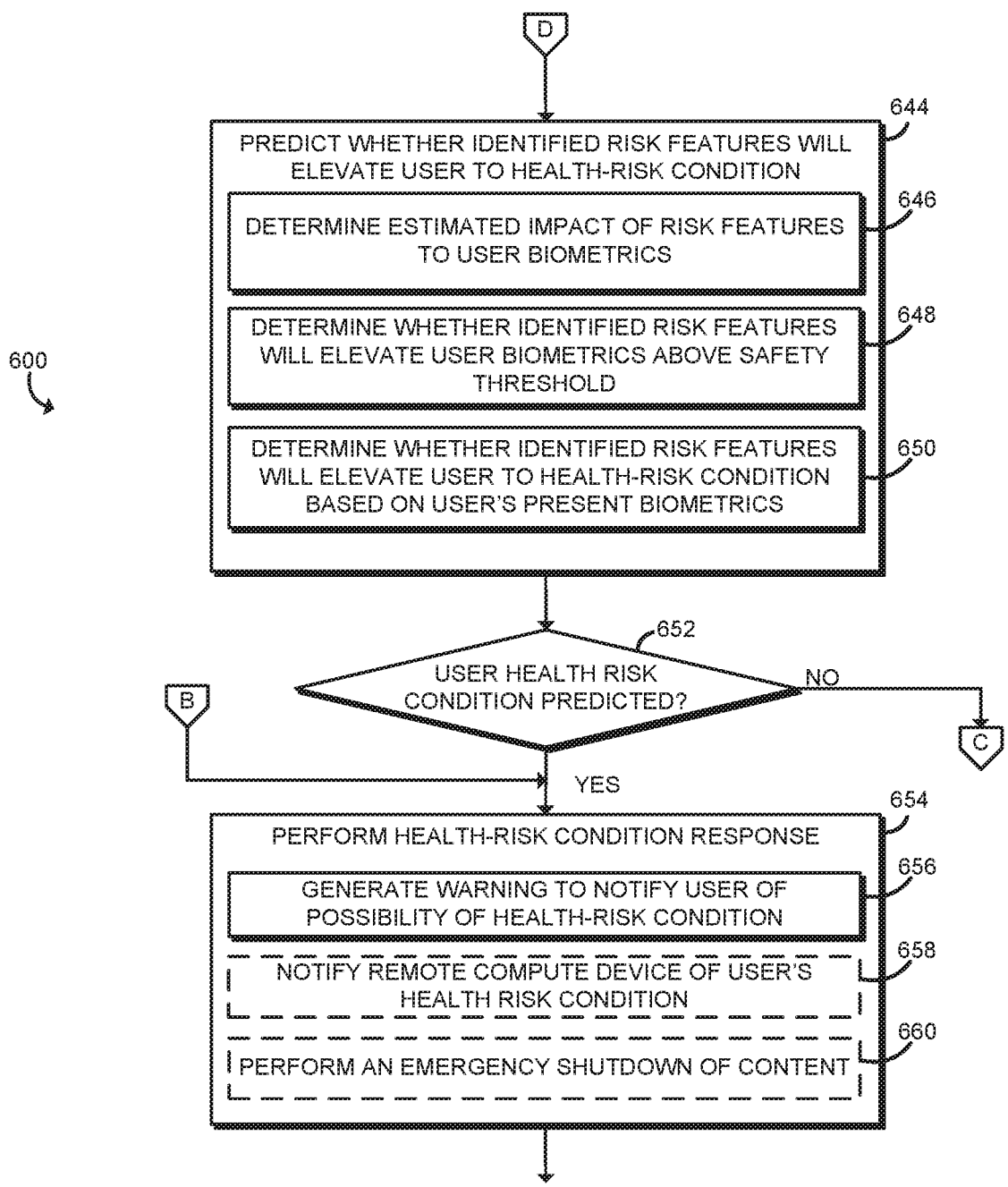

Referring now to FIGS. 6-8, in use, the virtual reality compute device 102 may execute a method 600 for monitoring a health-risk condition of a user of the virtual reality compute device 102. The method 600 begins with block 602 in which the virtual reality compute device 102 determines whether to present the VR presentation to the user. To do so, the virtual reality compute device 102 may wait to receive an input from the user, such as a selection of a VR presentation that may include but is not limited to movies, videos, video games and the like. If it is determined that the virtual reality compute device 102 is to present the VR, presentation, the method 600 advances to block 604. However, if it is determined that the virtual reality compute device 102 is not to present a VR presentation, the method 600 loops back to the start of block 602.

In block 604, the virtual reality compute device 102 determines a user baseline biometrics. Such determination establishes safety thresholds for the user biometrics. To do so, in some embodiments, in block 606, the virtual reality compute device 102 retrieves baseline biometrics from the data storage 318. The baseline biometrics may include a heart rate baseline, blood pressure baseline, hypertension baseline, etc. as described above. Other baselines may be included to properly determine whether a user is in a health-risk condition. In addition, in some embodiments, in block 608, the virtual reality compute device 102 may receive user-identified risk factors for a health-risk condition. The user-identified risk factors may include information such as whether the user has experienced a previous heart attack, has hypertension, etc. as described above. The user-identified risk factors allows for the virtual reality compute device 102 to adjust safety thresholds and/or to properly respond to certain conditions in order to ensure the safety of the user.

Subsequently to determining the user baseline biometrics, the virtual reality compute device 102 presents the selected VR presentation to the user in block 610. While the virtual reality compute device 102 presents the VR presentation, the virtual reality compute device 102 determines the user's present monitored biometrics in block 612. For example, in block 614, the virtual reality compute device 102 determines the user's heart rate. To do so, in block 616, the virtual reality compute device 102 retrieves or otherwise obtains sensor data indicative of heart rate from the NIR sensor(s) 310. Additionally, in block 618, the virtual reality compute device 102 determines the user's blood pressure. To do so, in block 620, the virtual reality compute device 102 retrieves or otherwise obtains sensor data indicative of blood pressure from the NIR(s) 310. The determination of the heart rate and blood pressure in blocks 614 and 618 provides a current perspective on the condition of the user in relation to the content presented in the VR presentation.

After the virtual reality compute device 102 determines the user's present monitored biometrics, the method 600 proceeds to block 622 of FIG. 7 in which the virtual reality compute device 102 determines whether the user is in a health-risk condition based on measured biometrics. To do so, the virtual reality compute device 102 determines whether the user's measured biometrics exceed a safety threshold associated with each particular biometric. For example, in block 624, the virtual reality compute device 102 determines whether the user is in a health-risk condition based on a determined heart rate. To do so, in block 626, the virtual reality compute device 102 determines whether the user is in a health-risk condition based on a determined heart rate by comparing the determined heart rate to a heart rate safety threshold determined based on the user's baseline biometrics determined via method 500 discussed above.

Furthermore, in block 628, the virtual reality compute device 102 determines whether the user is in a health-risk condition based on the determined blood pressure. To do so, in block 630, the virtual reality compute device 102 compares the determined blood pressure to a blood pressure safety threshold determined based on the user's baseline biometrics as discussed above. Additionally in some embodiments in block 632, the virtual reality compute device 102 determines a hypertension grade based on the user's determined blood pressure. The virtual reality compute device 102 may subsequently determine whether the hypertension grade identifies the user in a health-risk condition.

In block 634, the virtual reality compute device 102 determines whether a health-risk condition has been detected. If it is determined that there is a health-risk condition detected, the method 600 branches ahead to block 654 of FIG. 8. If it is determined that there is no health-risk condition, the method 600 advances to block 636 in which the virtual reality compute device 102 performs a determination of whether to analyze the content of the VR presentation for future health-risks (i.e., whether to "look ahead" in the VR content for possible health-risks). If it is determined the virtual reality compute device 102 does not need to analyze the content for future health-risks, the method 600 returns to block 610 of FIG. 6 in which the virtual reality compute device 102 continues to present VR presentations to the user. If it is determined that the virtual reality compute device 102 needs to analyze the content for future health-risks, the method advances to block 638.

In block 638, the virtual reality compute device 102 analyzes future content of the VR presentation (i.e., content of the VR presentation not yet presented to the user) to identify risk features that may elevate user biometrics as described above. In some embodiments, in block 640, the virtual reality compute device 102 analyzes future content based on a temporal window. The temporal window may have any length of time suitable to detect risk features that may elevate user biometrics in a suitable amount of time to allow the virtual reality compute device 102 to react to any identified risk features. For example, the temporal window may be at least 5 minutes in some embodiments. Alternatively, in some embodiments, in block 642, the virtual reality compute device 102 analyzes the entirety of the VR presentation to detect risk features that may elevate the user biometrics.

After analyzing the future content of the VR presentation in block 638, the method 600 proceeds to block 644 of FIG. 8. In block 644, the virtual reality compute device 102 predicts whether the identified risk features will elevate the user to a health-risk condition. To do so, in block 646, the virtual reality compute device 102 determines an estimated impact of risk features to the user's biometric measurements. In particular, in block 648, the virtual reality compute device 102 determines whether the identified risk features will elevate the user biometrics above the corresponding safety threshold as described above. For example, the virtual reality compute device 102 determines whether the identified risk features will elevate the user's heart rate above a heart rate safety threshold and/or the user's blood pressure above a blood pressure safety threshold. In some embodiments, the virtual reality compute device 102 may determine whether the identified risk features lowers the user's heart rate and/or blood pressure below a respective safety threshold. Furthermore, in block 650, the virtual reality compute device 102 determines whether the identified risk features will elevate the user to a health-risk condition based on the user's present biometrics and the predicted impact to such biometrics. For example, the virtual reality compute device 102 may determine whether the identified risk features would be enough to elevate the user's present biometrics above the safety threshold, such as a heart rate above the heart rate safety threshold. Such may be the case if the present user biometrics are relatively high and the identified risk features is predicted to elevate the heart rate or blood pressure even higher, resulting in a predicted heart rate and/or blood pressure above the corresponding safety threshold.

In block 652, the virtual reality compute device 102 determines whether a user health-risk condition has been predicted. If the virtual reality compute device 102 determined there is no health-risk condition predicted, the method 600 returns to block 610 of FIG. 6 to continue presenting the VR presentation to the user.

If, however, the virtual reality compute device 102 has predicted a possible future a health-risk condition in block 652 or if an existing health-risk condition of the user has already been detected in block 634 (see FIG. 7), the method 600 advances to block 654. In block 654, the virtual reality compute device 102 performs a health-risk condition response. The health-risk condition response may be embodied as a preemptive action or an action to address a current health-risk condition. For example, in block 656, the virtual reality compute device 102 may generate a warning to notify the user of the existence of or the possibility of a health-risk condition. Furthermore, in some embodiments, in block 658, the virtual reality compute device 102 notifies a remote compute device of the user's health-risk condition. Such a notification may provide additional awareness to other individuals in case the health-risk condition causes the user to become unconscious, thereby providing quick assistance to the user. In addition, in some embodiments, in block 660, the virtual reality compute device 102 performs an emergency shutdown of the VR presentation to stop the presentation of the content to the user. Additionally or alternatively, in some embodiments, the virtual reality compute device 102 may display a neutral or calming display to lower the user's heart rate or blood pressure. Regardless, after performing the health-risk condition response, the method 600 is completed.

EXAMPLES

Illustrative examples of the technologies disclosed herein are provided below. An embodiment of the technologies may include any one or more, and any combination of, the examples described below.

Example 1 includes a virtual reality compute device for monitoring a health-risk condition of a user, the virtual reality compute device comprising a content manager to present a virtual reality (VR) presentation to the user; one or more near infrared (NIR) sensors to produce sensor data indicative of a heart rate of the user and a blood pressure of the user while the VR presentation is presented to the user; a physical condition determination manager to determine whether the user is in a health-risk condition based on a comparison of the heart rate of the user to a heart rate safety threshold and a comparison of the blood pressure of the user to a blood pressure safety threshold; and a warning generator to perform a health-risk condition response in response to a determination that the user is in the health-risk condition.

Example 2 includes the subject matter of Example 1, and further including a NIR sensor manager to determine a hypertension grade of the user based on the sensor data indicative of the blood pressure of the user produced by the NIR sensor.

Example 3 includes the subject matter of any of Examples 1 and 2, and wherein the physical condition determination manager is to determine whether the user is in the health-risk condition based on a comparison of the hypertension grade of the user to a hypertension grade safety threshold.

Example 4 includes the subject matter of any of Examples 1-3, and further including a user baseline biometrics manager to determine at least one of a heart rate baseline or a blood pressure baseline.

Example 5 includes the subject matter of any of Examples 1-4, and wherein to determine the at least one of the heart rate baseline or the blood pressure baseline comprises at least one of (i) to monitor the heart rate of the user to determine the heart rate baseline or (ii) to monitor the blood pressure of the user to determine the blood pressure baseline.

Example 6 includes the subject matter of any of Examples 1-5, and wherein the baseline biometrics manager is further to store the at least one of the heart rate baseline or the blood pressure baseline in a data storage of the virtual reality compute device.

Example 7 includes the subject matter of any of Examples 1-6, and wherein to determine the at least one of the heart rate baseline or the blood pressure baseline comprises to receive baseline parameters from the user.

Example 8 includes the subject matter of any of Examples 1-7, and wherein the content manager is to present the VR presentation to the user via a display of the virtual reality compute device.

Example 9 includes the subject matter of any of Examples 1-8, and wherein the content manager is further to analyze future content of the VR presentation that has not yet been presented to the user to identify risk features that will elevate user biometrics.

Example 10 includes the subject matter of any of Examples 1-9, and wherein to analyze the future content comprises to analyze the future content based on at least one temporal window applied to the VR presentation.

Example 11 includes the subject matter of any of Examples 1-10, and wherein the at least one temporal window comprises at least a next five minutes of the VR presentation.

Example 12 includes the subject matter of any of Examples 1-11, and wherein to analyze the future content comprises to analyze the entirety of the VR presentation.

Example 13 includes the subject matter of any of Examples 1-12, and wherein the content manager is further to predict whether the identified risk features will elevate the user to the health-risk condition.

Example 14 includes the subject matter of any of Examples 1-13, and wherein to predict whether the identified risk features will elevate the user to the health-risk condition comprises to determine an estimated impact of the risk features to the heart rate of the user or the blood pressure of the user.

Example 15 includes the subject matter of any of Examples 1-14, and wherein to predict whether the identified risk features will elevate the user to the health-risk condition comprises to determine whether the identified risk features will elevate (i) the heart rate of the user above the heart rate safety threshold or (ii) the blood pressure of the user above the blood pressure safety threshold.

Example 16 includes the subject matter of any of Examples 1-15, and wherein to predict whether the identified risk features will elevate the user to the health-risk condition comprises to determine whether identified risk factors will elevate the user to the health-risk condition based on the user's present heart rate or blood pressure.

Example 17 includes the subject matter of any of Examples 1-16, and wherein to perform the health-risk condition response comprises to generate a warning to notify the user of a possibility of the health-risk condition.

Example 18 includes the subject matter of any of Examples 1-17, and wherein to perform the health-risk condition response comprises to notify a remote compute device that the user is in the health-risk condition.

Example 19 includes the subject matter of any of Examples 1-18, and wherein to perform the health-risk condition response comprises to perform an emergency shutdown of the VR presentation.

Example 20 includes the subject matter of any of Examples 1-19, and wherein the content manager is further to display at least one of a neutral or calming presentation to the user to deescalate the user biometrics.

Example 21 includes a method for monitoring a health-risk condition of a user, the method comprising presenting, by a virtual reality compute device, a virtual reality (VR) presentation to the user of the virtual reality compute device; producing, by one or more near infrared (NIR) sensors of the virtual reality compute device, sensor data indicative of a heart rate of the user and a blood pressure of the user while the VR presentation is presented to the user; determining, by the virtual reality compute device, whether the user is in the health-risk condition based on a comparison of the heart rate of the user to a heart rate safety threshold and a comparison of the blood pressure of the user to a blood pressure safety threshold; and performing, by the virtual reality compute device, a health-risk condition response in response to determining that the user is in the health-risk condition.

Example 22 includes the subject matter of Example 21, and further including determining, by the virtual reality compute device, a hypertension grade of the user based on the sensor data indicative of the blood pressure of the user by the NIR sensor.

Example 23 includes the subject matter of any of Examples 21 and 22, and further including determining, by the virtual reality compute device, whether the user is in the health-risk condition based on a comparison of the hypertension grade of the user to a hypertension grade safety threshold.

Example 24 includes the subject matter of any of Examples 21-23, and further including determining, by the virtual reality compute device, at least one of a heart rate baseline or a blood pressure baseline.

Example 25 includes the subject matter of any of Examples 21-24, and wherein determining the at least one of the heart rate baseline or the blood pressure baseline comprises at least one of (i) monitoring the heart rate of the user to determine the heart rate baseline or (ii) monitoring the blood pressure of the user to determine the blood pressure baseline.

Example 26 includes the subject matter of any of Examples 21-25, and further including storing, by the virtual reality compute device, the at least one of the heart rate baseline or the blood pressure baseline in a data storage of the virtual reality compute device.

Example 27 includes the subject matter of any of Examples 21-26, and wherein determining the at least one of the heart rate baseline or the blood pressure baseline comprises receiving baseline parameters from the user.

Example 28 includes the subject matter of any of Examples 21-27, and wherein presenting the VR presentation to the user comprises presenting the VR presentation to the user via a display of the virtual reality compute device.

Example 29 includes the subject matter of any of Examples 21-28, and further including analyzing, by the virtual reality compute device, future content of the VR presentation that has not yet been presented to the user to identify risk features that will elevate user biometrics.

Example 30 includes the subject matter of any of Examples 21-29, and wherein analyzing the future content comprises analyzing the future content based on at least one temporal window applied to the VR presentation.

Example 31 includes the subject matter of any of Examples 21-30, and wherein the at least one temporal window comprises at least a next five minutes of the VR presentation.

Example 32 includes the subject matter of any of Examples 21-31, and wherein analyzing the future content comprises analyzing the entirety of the VR presentation.

Example 33 includes the subject matter of any of Examples 21-32, and further including predicting, by the virtual reality compute device, whether the identified risk features will elevate the user to the health-risk condition.

Example 34 includes the subject matter of any of Examples 21-33, and wherein predicting whether the identified risk features will elevate the user to the health-risk condition comprises determining an estimated impact of the risk features to the heart rate of the user or the blood pressure of the user.

Example 35 includes the subject matter of any of Examples 21-34, and wherein predicting whether the identified risk features will elevate the user to the health-risk condition comprises determining whether the identified risk features will elevate (i) the heart rate of the user above the heart rate safety threshold or (ii) the blood pressure of the user above the blood pressure safety threshold.

Example 36 includes the subject matter of any of Examples 21-35, and wherein predicting whether the identified risk features will elevate the user to the health-risk condition comprises determining whether identified risk factors will elevate the user to the health-risk condition based on the user's present heart rate or blood pressure.

Example 37 includes the subject matter of any of Examples 21-36, and wherein performing the health-risk condition response comprises generating a warning notifying the user of a possibility of the health-risk condition.

Example 38 includes the subject matter of any of Examples 21-37, and wherein performing the health-risk condition response comprises notifying a remote compute device that the user is in the health-risk condition.

Example 39 includes the subject matter of any of Examples 21-38, and wherein performing the health-risk condition response comprises performing an emergency shutdown of the VR presentation.

Example 40 includes the subject matter of any of Examples 21-39, and further including displaying, by the virtual reality compute device, at least one of a neutral or calming presentation to the user to deescalate the user biometrics.

Example 41 includes a compute device comprising a processor; and a memory having stored therein a plurality of instructions that when executed by the processor cause the compute device to perform the method of any of Examples 21-40.

Example 42 includes one or more machine readable storage media comprising a plurality of instructions stored thereon that in response to being executed result in a compute device performing the method of any of Examples 21-40.

Example 43 includes a virtual reality compute device for monitoring a health-risk condition of a user, the virtual reality compute device comprising means for presenting a virtual reality (VR) presentation to the user of the virtual reality compute device; means for producing sensor data indicative of a heart rate of the user and a blood pressure of the user while the VR presentation is presented to the user; means for determining whether the user is in the health-risk condition based on a comparison of the heart rate of the user to a heart rate safety threshold and a comparison of the blood pressure of the user to a blood pressure safety threshold; and means for performing a health-risk condition response in response to determining that the user is in the health-risk condition.

Example 44 includes the subject matter of any of Examples 42 and 43, and further including means for determining a hypertension grade of the user based on the sensor data indicative of the blood pressure of the user.

Example 45 includes the subject matter of any of Examples 42-44, and further including means for determining whether the user is in the health-risk condition based on a comparison of the hypertension grade of the user to a hypertension grade safety threshold.

Example 46 includes the subject matter of any of Examples 42-45, and further including means for determining at least one of a heart rate baseline or a blood pressure baseline.

Example 47 includes the subject matter of any of Examples 42-46, and wherein determining the at least one of the heart rate baseline or the blood pressure baseline comprises at least one of (i) monitoring the heart rate of the user to determine the heart rate baseline or (ii) monitoring the blood pressure of the user to determine the blood pressure baseline.

Example 48 includes the subject matter of any of Examples 42-47, and further including means for storing the at least one of the heart rate baseline or the blood pressure baseline in a data storage of the virtual reality compute device.

Example 49 includes the subject matter of any of Examples 42-48, and wherein determining the at least one of the heart rate baseline or the blood pressure baseline comprises receiving baseline parameters from the user.

Example 50 includes the subject matter of any of Examples 42-49, and further including means for analyzing future content of the VR presentation that has not yet been presented to the user to identify risk features that will elevate user biometrics.

Example 51 includes the subject matter of any of Examples 42-50, and wherein analyzing the future content comprises analyzing the future content based on at least one temporal window applied to the VR presentation.

Example 52 includes the subject matter of any of Examples 42-51, and wherein the at least one temporal window comprises at least a next five minutes of the VR presentation.

Example 53 includes the subject matter of any of Examples 42-52, and wherein analyzing the future content comprises analyzing the entirety of the VR presentation.

Example 54 includes the subject matter of any of Examples 42-53, and further including means for predicting whether the identified risk features will elevate the user to the health-risk condition.

Example 55 includes the subject matter of any of Examples 42-54, and wherein predicting whether the identified risk features will elevate the user to the health-risk condition comprises determining an estimated impact of the risk features to the heart rate of the user or the blood pressure of the user.

Example 56 includes the subject matter of any of Examples 42-55, and wherein predicting whether the identified risk features will elevate the user to the health-risk condition comprises determining whether the identified risk features will elevate (i) the heart rate of the user above the heart rate safety threshold or (ii) the blood pressure of the user above the blood pressure safety threshold.

Example 57 includes the subject matter of any of Examples 42-56, and wherein predicting whether the identified risk features will elevate the user to the health-risk condition comprises determining whether identified risk factors will elevate the user to the health-risk condition based on the user's present heart rate or blood pressure.

Example 58 includes the subject matter of any of Examples 42-57, and wherein performing the health-risk condition response comprises generating a warning notifying the user of a possibility of the health-risk condition.

Example 59 includes the subject matter of any of Examples 42-58, and wherein performing the health-risk condition response comprises notifying a remote compute device that the user is in the health-risk condition.

Example 60 includes the subject matter of any of Examples 42-59, and wherein performing the health-risk condition response comprises performing an emergency shutdown of the VR presentation.

Example 61 includes the subject matter of any of Examples 42-60, and further including means for displaying at least one of a neutral or calming presentation to the user to deescalate the user biometrics.

The invention claimed is:

1. A virtual reality device for monitoring a health-risk condition of a user, the virtual reality device comprising:
one or more near infrared (NIR) sensors to produce sensor data indicative of a heart rate of the user and a blood pressure of the user while a Virtual reality (VR) presentation is presented to the user;
machine-readable instructions; and
processor circuitry to execute the instructions to:
determine whether the user is in a health-risk condition based on a comparison of the heart rate of the user to a heart rate safety threshold and a comparison of the blood pressure of the user to a blood pressure safety threshold;
perform a health-risk condition response in response to the determination that the user is in the health-risk condition; and
analyze content of the VR presentation that has not yet been presented to the user to identify a portion of the content associated with elevated user biometrics.

2. The virtual reality device of claim 1, wherein the processor circuitry is to:
determine a hypertension grade of the user based on the sensor data indicative of the blood pressure of the user produced by the NIR sensor; and
determine whether the user is in the health-risk condition based on a comparison of the hypertension grade of the user to a hypertension grade safety threshold.

3. The virtual reality device of claim 1, wherein the processor circuitry is to:
determine a heart rate baseline;
determine a blood pressure baseline;
store the heart rate baseline and the blood pressure baseline in a data storage of the virtual reality device;
determine the heart rate safety threshold on the heart rate baseline; and
determine the blood pressure safety threshold on the blood pressure deadline.

4. The virtual reality device of claim 3, wherein the processor circuitry is to:
monitor the heart rate of the user over time and average the heart rate of the user to determine the heart rate baseline; and
monitor the blood pressure of the user over time and average the blood pressure of the user to determine the blood pressure baseline.

5. The virtual reality device of claim 1, wherein the processor circuitry is to present the VR presentation to the user via a display of the virtual reality device.

6. The virtual reality device of claim 5, wherein the processor circuitry is to:
divide the VR presentation into temporal windows; and
analyze the content of the VR presentation that has not yet been presented in successive stages based on the temporal windows.

7. The virtual reality device of claim 5, wherein the processor circuitry is to identify the portion of the content associated with elevated user biometrics based on the portion of the content including at least one of an increase in volume, a dynamic event, or a change in a light level.

8. The virtual reality device of claim 5 wherein to identify the portion of the content associated with elevated user biometrics, the processor circuitry is to determine whether the identified portion of the content will elevate at least one of (i) the heart rate of the user above the heart rate safety threshold or (ii) the blood pressure of the user above the blood pressure safety threshold.

9. The virtual reality device of claim 1, wherein to perform the health-risk condition response, the processor circuitry is to at least one of: generate a warning to notify the user of a possibility of the health-risk condition, notify a remote compute device that the user is in the health-risk condition, or perform an emergency shutdown of the VR presentation.

10. A method for monitoring a health-risk condition of a user, the method comprising:
presenting, by a virtual reality device, a virtual reality (VR) presentation to the user of the virtual reality device;
producing, by one or more near infrared (NIR) sensors of the virtual reality device, sensor data indicative of a heart rate of the user and a blood pressure of the user while the VR presentation is presented to the user;
determining, by the virtual reality device, whether the user is in the health-risk condition based on a comparison of the heart rate of the user to a heart rate safety threshold and a comparison of the blood pressure of the user to a blood pressure safety threshold;
performing, by the virtual reality device, a health-risk condition response in response to determining that the user is in the health-risk condition; and
analyzing, by the virtual reality device, content of the VR presentation that has not yet been presented to the user to identify a portion of the content associated with elevated user biometrics.

11. The method of claim 10, further including:
determining, by the virtual reality device, a hypertension grade of the user based on the sensor data indicative of the blood pressure of the user by the NIR sensor; and
determining, by the virtual reality device, whether the user is in the health-risk condition based on a comparison of the hypertension grade of the user to a hypertension grade safety threshold.

12. The method of claim 10, further including:
determining, by the virtual reality device, at least one of a heart rate baseline or a blood pressure baseline;
storing, by the virtual reality device, the at least one of the heart rate baseline or the blood pressure baseline in a data storage of the virtual reality compute device; and
determining, by the virtual reality device, at least one of the heart rate safety threshold on the heart rate baseline or the blood pressure safety threshold on the blood pressure deadline.

13. The method of claim 12, wherein the determining of the at least one of the heart rate baseline or the blood pressure baseline includes at least one of: (i) monitoring the heart rate of the user to determine the heart rate baseline or (ii) monitoring the blood pressure of the user to determine the blood pressure baseline.

14. The method of claim 10, wherein the analyzing of the content of the VR presentation that has not yet been presented to the user includes:
   dividing the VR presentation into temporal windows; and
   analyzing the content of the VR presentation that has not yet been presented in successive stages based on the temporal windows.

15. The method of claim 10, wherein the predicting whether the content will elevate the biometrics is based on at least one of an increase in volume, a dynamic event, or a change in a light level.

16. The method of claim 10, further including predicting whether the content will elevate at least one of (i) the heart rate of the user above the heart rate safety threshold or (ii) the blood pressure of the user above the blood pressure safety threshold.

17. The method of claim 10, wherein performing the health-risk condition response includes at least one of generating a warning notifying the user of a possibility of the health-risk condition, notifying a remote compute device that the user is in the health-risk condition, or performing an emergency shutdown of the VR presentation.

18. One or more machine readable storage device comprising instructions that in response to being executed cause a computing device to:
   cause presentation of a virtual reality (VR) presentation to the user;
   obtain sensor data indicative of a heart rate of the user and a blood pressure of the user while the VR presentation is presented to the user;
   analyze content of the VR presentation that has not yet been presented to the user to identify a portion of the content associated with elevated user biometrics;
   determine whether the user is in a health-risk condition based on a comparison of the heart rate of the user to a heart rate safety threshold and a comparison of the blood pressure of the user to a blood pressure safety threshold;
   determine whether the user may be approaching a health-risk condition based on the analysis of the content of the VR presentation that has not yet been presented to the user; and
   perform a health-risk condition response in response to either a determination that the user is in the health-risk condition or that the user may be approaching a health-risk condition.

19. The one or more machine readable storage device of claim 18, wherein the instructions cause the computing device to:
   determine a hypertension grade of the user based on the sensor data indicative of the blood pressure of the user; and
   determine whether the user is in the health-risk condition based on a comparison of the hypertension grade of the user to a hypertension grade safety threshold.

20. The one or more machine readable storage device of claim 18, wherein the instructions cause the computing device to:
   determine at least one of a heart rate baseline or a blood pressure baseline; and
   store the at least one of the heart rate baseline or the blood pressure baseline in a data storage of the virtual reality compute device.

21. The one or more machine readable storage device of claim 20, wherein to determine the at least one of the heart rate baseline or the blood pressure baseline, the instructions cause the computing device to at least one of: (i) to monitor the heart rate of the user to determine the heart rate baseline or (ii) to monitor the blood pressure of the user to determine the blood pressure baseline.

22. The one or more machine readable storage device of claim 18, wherein to analyze future content of the VR presentation that has not yet been presented to the user, the instructions cause the computing device to:
   divide the VR presentation into temporal windows; and
   analyze the content of the VR presentation that has not yet been presented in successive stages based on the temporal windows.

23. The one or more machine readable storage device of claim 18, wherein the instructions cause the computing device to identify the portion of the content associated with elevated user biometrics based on at least one of an increase in volume, a dynamic event, or a change in a light level.

24. The one or more machine readable storage device of claim 18, wherein the instructions cause the computing device to predict whether the content will elevate at least one of (i) the heart rate of the user above the heart rate safety threshold or (ii) the blood pressure of the user above the blood pressure safety threshold.

25. The one or more machine readable storage device of claim 18, wherein to perform the health-risk condition response, the instructions cause the computing device to at least one of generate a warning to notify the user of a possibility of the health-risk condition, notify a remote compute device that the user is in the health-risk condition, or perform an emergency shutdown of the VR presentation.

* * * * *

UNITED STATES PATENT AND TRADEMARK OFFICE
CERTIFICATE OF CORRECTION

PATENT NO. : 11,571,133 B2
APPLICATION NO. : 16/642561
DATED : February 7, 2023
INVENTOR(S) : Peng et al.

Page 1 of 1

It is certified that error appears in the above-identified patent and that said Letters Patent is hereby corrected as shown below:

In the Claims

Column 21, in Claim 15, delete "15. The method of claim 10, wherein the predicting whether the content will elevate the biometrics is based on at least one of an increase in volume, a dynamic event, or a change in a light level.", and insert -- 15. The method of claim 10, further including predicting whether the content will elevate at least one of (i) the heart rate of the user above the heart rate safety threshold or (ii) the blood pressure of the user above the blood pressure safety threshold. --

Column 21, in Claim 16, delete "16. The method of claim 10, further including predicting whether the content will elevate at least one of (i) the heart rate of the user above the heart rate safety threshold or (ii) the blood pressure of the user above the blood pressure safety threshold.", and insert -- 16. The method of claim 15, wherein the predicting whether the content will elevate the biometrics is based on at least one of an increase in volume, a dynamic event, or a change in a light level. --

Signed and Sealed this
Fourth Day of April, 2023

Katherine Kelly Vidal
*Director of the United States Patent and Trademark Office*